US007455907B2

(12) United States Patent
Pacetti et al.

(10) Patent No.: US 7,455,907 B2
(45) Date of Patent: *Nov. 25, 2008

(54) HYDROPHOBIC BIOLOGICALLY ABSORBABLE COATINGS FOR DRUG DELIVERY DEVICES AND METHODS FOR FABRICATING THE SAME

(75) Inventors: Stephen D. Pacetti, San Jose, CA (US); Syed F. A. Hossainy, Fremont, CA (US)

(73) Assignee: Advanced Cardiovascular Systems Inc., Santa Clara, CA (US)

( * ) Notice: Subject to any disclaimer, the term of this patent is extended or adjusted under 35 U.S.C. 154(b) by 3 days.

This patent is subject to a terminal disclaimer.

(21) Appl. No.: 11/402,392

(22) Filed: Apr. 11, 2006

(65) Prior Publication Data

US 2006/0182782 A1   Aug. 17, 2006

Related U.S. Application Data

(63) Continuation of application No. 10/630,250, filed on Jul. 30, 2003, now Pat. No. 7,056,591.

(51) Int. Cl.
*A61F 2/02* (2006.01)
*A61F 2/06* (2006.01)
*B32B 27/00* (2006.01)
*B32B 27/36* (2006.01)

(52) U.S. Cl. .................. 428/411.1; 428/480; 623/1.46; 623/1.49

(58) Field of Classification Search ............... 428/411.1, 428/480; 623/1.46, 1.49
See application file for complete search history.

(56) References Cited

U.S. PATENT DOCUMENTS

| | | | |
|---|---|---|---|
| 4,079,038 A | 3/1978 | Choi et al. | |
| 4,304,767 A | 12/1981 | Heller et al. | |
| 4,329,383 A | 5/1982 | Joh | |
| 4,733,665 A | 3/1988 | Palmaz | |
| 4,800,882 A | 1/1989 | Gianturco | |
| 4,882,168 A | 11/1989 | Casey et al. | |
| 4,886,062 A | 12/1989 | Wiktor | |
| 4,941,870 A | 7/1990 | Okada et al. | |
| 4,977,901 A | 12/1990 | Ofstead | |
| 5,112,457 A | 5/1992 | Marchant | |
| 5,165,919 A | 11/1992 | Sasaki et al. | |
| 5,272,012 A | 12/1993 | Opolski | |
| 5,292,516 A | 3/1994 | Viegas et al. | |
| 5,298,260 A | 3/1994 | Viegas et al. | |
| 5,300,295 A | 4/1994 | Viegas et al. | |
| 5,306,501 A | 4/1994 | Viegas et al. | |
| 5,328,471 A | 7/1994 | Slepian | |
| 5,330,768 A | 7/1994 | Park et al. | |
| 5,380,299 A | 1/1995 | Fearnot et al. | |
| 5,417,981 A | 5/1995 | Endo et al. | |
| 5,447,724 A | 9/1995 | Helmus et al. | |
| 5,455,040 A | 10/1995 | Marchant | |
| 5,462,990 A | 10/1995 | Hubbell et al. | |
| 5,464,650 A | 11/1995 | Berg et al. | |
| 5,569,463 A | 10/1996 | Helmus et al. | |
| 5,578,073 A | 11/1996 | Haimovich et al. | |
| 5,581,387 A | 12/1996 | Cahill | |
| 5,605,696 A | 2/1997 | Eury et al. | |
| 5,609,629 A | 3/1997 | Fearnot et al. | |
| 5,624,411 A | 4/1997 | Tuch | |
| 5,628,730 A | 5/1997 | Shapland et al. | |
| 5,649,977 A | 7/1997 | Campbell | |
| 5,658,995 A | 8/1997 | Kohn et al. | |
| 5,667,767 A | 9/1997 | Greff et al. | |
| 5,670,558 A | 9/1997 | Onishi et al. | |
| 5,679,400 A | 10/1997 | Tuch | |
| 5,700,286 A | 12/1997 | Tartaglia et al. | |
| 5,702,754 A | 12/1997 | Zhong | |
| 5,716,981 A | 2/1998 | Hunter et al. | |
| 5,735,897 A | 4/1998 | Buirge | |
| 5,746,998 A | 5/1998 | Torchilin et al. | |
| 5,776,184 A | 7/1998 | Tuch | |
| 5,788,979 A | 8/1998 | Alt et al. | |
| 5,800,392 A | 9/1998 | Racchini | |
| 5,820,917 A | 10/1998 | Tuch | |
| 5,824,048 A | 10/1998 | Tuch | |
| 5,824,049 A | 10/1998 | Ragheb et al. | |
| 5,830,178 A | 11/1998 | Jones et al. | |
| 5,837,008 A | 11/1998 | Berg et al. | |
| 5,837,313 A | 11/1998 | Ding et al. | |
| 5,851,508 A | 12/1998 | Greff et al. | |
| 5,858,746 A | 1/1999 | Hubbell et al. | |

(Continued)

FOREIGN PATENT DOCUMENTS

| | | |
|---|---|---|
| EP | 0 301 856 | 2/1989 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |

(Continued)

OTHER PUBLICATIONS

U.S. Appl. No. 10/630,250, filed Jul. 30, 2002, Pacetti et al.
U.S. Appl. No. 10/718,278, filed Nov. 19, 2003, Hossainy et al.
U.S. Appl. No. 10/719,516, filed Nov. 21, 2003, Tang et al.
U.S. Appl. No. 10/738,704, filed Dec. 16, 2003, Pacetti et al.
U.S. Appl. No. 10/741,214, filed Dec. 19, 2003, Pacetti et al.

(Continued)

*Primary Examiner*—Ramsey Zacharia
(74) *Attorney, Agent, or Firm*—Squire, Sanders & Dempsey L.L.P.

(57) ABSTRACT

A polymer coating for medical devices based on polyorthoesters and methods for fabricating the coating are disclosed.

19 Claims, No Drawings

U.S. PATENT DOCUMENTS

| | | | |
|---|---|---|---|
| 5,861,387 A | 1/1999 | Labrie et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,925,720 A | 7/1999 | Kataoka et al. |
| 5,955,509 A | 9/1999 | Webber et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,015,541 A | 1/2000 | Greff et al. |
| 6,033,582 A | 3/2000 | Lee et al. |
| 6,042,875 A | 3/2000 | Ding et al. |
| 6,051,576 A | 4/2000 | Ashton et al. |
| 6,051,648 A | 4/2000 | Rhee et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,536 A | 9/2000 | Ding et al. |
| 6,120,904 A | 9/2000 | Hostettler et al. |
| 6,121,027 A | 9/2000 | Clapper et al. |
| 6,129,761 A | 10/2000 | Hubbell |
| 6,153,252 A | 11/2000 | Hossainy et al. |
| 6,165,212 A | 12/2000 | Dereume et al. |
| 6,203,551 B1 | 3/2001 | Wu |
| 6,231,600 B1 | 5/2001 | Zhong |
| 6,240,616 B1 | 6/2001 | Yan |
| 6,245,753 B1 | 6/2001 | Byun et al. |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,346,110 B2 | 2/2002 | Wu |
| 6,358,556 B1 | 3/2002 | Ding et al. |
| 6,379,381 B1 | 4/2002 | Hossainy et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,527,801 B1 | 3/2003 | Dutta |
| 6,527,863 B1 | 3/2003 | Pacetti et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,765 B1 | 7/2003 | Hossainy et al. |
| 6,585,926 B1 | 7/2003 | Mirzaee |
| 6,605,154 B1 | 8/2003 | Villareal |
| 6,703,040 B2 | 3/2004 | Katsarava et al. |
| 2001/0018469 A1 | 8/2001 | Chen et al. |
| 2001/0037145 A1 | 11/2001 | Guruwaiya et al. |
| 2002/0077693 A1 | 6/2002 | Barclay et al. |
| 2002/0091433 A1 | 7/2002 | Ding et al. |
| 2002/0155212 A1 | 10/2002 | Hossainy |
| 2002/0168336 A1* | 11/2002 | Ng et al. .................. 424/78.38 |
| 2003/0065377 A1 | 4/2003 | Davila et al. |
| 2003/0099712 A1 | 5/2003 | Jayaraman |

FOREIGN PATENT DOCUMENTS

| | | |
|---|---|---|
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| JP | 2001-190687 | 7/2001 |
| WO | WO 91/12846 | 9/1991 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

U.S. Appl. No. 10/750,139, filed Dec. 30, 2003, Desnoyer et al.
U.S. Appl. No. 10/805,036, filed Mar. 16, 2004, Pacetti.
U.S. Appl. No. 10/816,072, filed Mar. 31, 2004, Dugan et al.
U.S. Appl. No. 10/835,656, filed Apr. 30, 2004, Tang et al.
U.S. Appl. No. 10/855,294, filed May 26, 2004, Pacetti et al.
U.S. Appl. No. 10/960,381, filed Oct. 6, 2004, Desnoyer et al.
U.S. Appl. No. 10/975,247, filed Oct. 27, 2004, Desnoyer et al.
U.S. Appl. No. 10/976,551, filed Oct. 29, 2004, Desnoyer et al.
U.S. Appl. No. 10/999,391, filed Nov. 29, 2004, Hossainy.
U.S. Appl. No. 11/023,837, filed Dec. 27, 2004, Hossainy.
U.S. Appl. No. 11/027,955, filed Dec. 30, 2004, Hossainy et al.
U.S. Appl. No. 11/035,816, filed Jan. 14, 2005, Hossainy et al.
Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Engelberg I. et al., *Physico-Mechanical Properties of Degradable Polymers Used in Medical Applications: a Comparative Study*, Biomaterials, vol. 12 (Apr. 1991).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

De Lezo et al., *Intracoronary Ultrasound Assessment of Directional Coronary Atherectomy: Immediate and Follow-Up Findings*, JACC vol. 21, No. 2, (1993) pp. 298-307.

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Moreno et al., *Macrophage Infiltration Predicts Restenosis After Coronary Intervention in Patients with Unstable Angina*, Circulation, vol. 94, No. 12, (1996) pp. 3098-3102.

Nordrehaug et al., *A novel biocompatible coating applied to coronary stents*, EPO Heart Journal 14, p. 321 (P1694), Abstr. Suppl. (1993).

Oikawa et al., *Mechanisms of Acute Gain and Late Lumen Loss After Atherectomy in Different Preintervention Arterial Remodeling Patterns*, The Am. J. of Cardiology, vol. 89, (2002), pp. 505-510.

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Scully et al., *Effect of a heparan sulphate with high affinity for antithrombin III upon inactivation of thrombin and coagulation Factor Xa*, Biochem J. 262, (1989) pp. 651-658.

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Virmani et al., *Lessons From Sudden Coronary Death a Comprehensive Morphological Classification Scheme for Atherosclerotic Lesions*, Arterioscler Thromb Vasc Biol. (2000) pp. 1262-1275.

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

\* cited by examiner

HYDROPHOBIC BIOLOGICALLY ABSORBABLE COATINGS FOR DRUG DELIVERY DEVICES AND METHODS FOR FABRICATING THE SAME

CROSS-REFERENCE TO RELATED APPLICATION

This application is a continuation application of U.S. application No. 10/630,250, filed on Jul. 30, 2003 now U.S. Pat. No. 7,056,591.

BACKGROUND OF THE INVENTION

1. Field of the Invention

This invention is directed to coatings for implantable medical devices, such as drug eluting vascular stents.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain vascular patency.

Stents are used not only as a mechanical intervention but also as a vehicle for providing pharmacological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Pharmacological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer. Once the stent has been implanted at the treatment site, the therapeutic substance has a sustained release profile from the polymer.

Local administration of therapeutic agents via stents has shown some favorable results in reducing restenosis. However, the biological compatibility of stent coatings can be improved. One of the properties characterizing biocompatibility of stent coatings where the improvement is desirable, is the ability of the human body to absorb the coating.

Accordingly, there is a need to have stent coatings with improved biological compatibility. The embodiments of the present invention provide for polymers and combination of polymers for coating stents and other implantable medical devices, where the polymers forming the coatings are biologically compatible and absorbable.

SUMMARY

A medical article, comprising an implantable substrate having a coating deposited on the substrate is provided, the coating comprising a polymer, the polymer being a product of co-polycondensation of a diketene acetal and a diol. Diketene acetal can be selected a compound having formula (I) or (II):

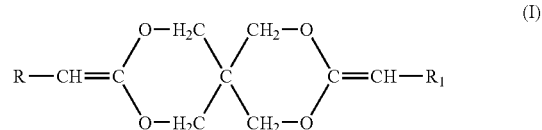

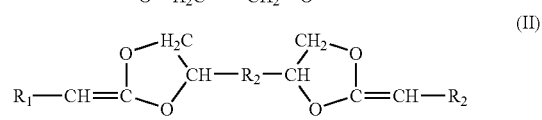

wherein R, $R_1$, $R_3$ and are, independently, unsubstituted or substituted straight-chained, branched, or cyclic alkyl radicals $C_1$-$C_8$, or unsubstituted or substituted aryl radicals; and $R_2$ is a straight chain or branched $C_1$ to $C_{16}$ alkyl group or a straight chain or branched $C_1$ to $C_{16}$ alkyl group containing an ether group. Examples of diketene acetals that can be used include 3,9-diethylidene-2,4,8,10-tetraoxaspiro-[5,5]-undecane, 3,9-dipentylidene-2,4,8,10-tetraoxaspiro-[5,5]-heptadecane, 3,9-dibutylidene-2,4,8,10-tetraoxaspiro-[5,5]-pentadecane, 3,9-dipropylidene-2,4,8,10-tetraoxaspiro-[5,5]-tridecane, and mixtures thereof. The coating can additionally include a second polymer that is a product of co-polycondensation of the diketene acetal, the diol, and a hydroxylated functional compound.

A medical device is provided. The medical article includes a coating comprising a polymer including a unit having a formula:

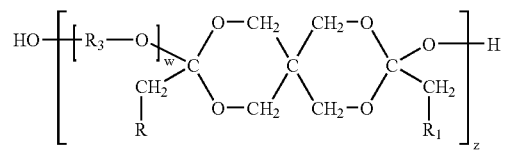

wherein R and $R_1$ are, independently, unsubstituted or substituted straight-chained, branched, or cyclic alkyl radicals $C_1$-$C_8$, or unsubstituted or substituted aryl radicals; $R_3$ is an aliphatic, cycloaliphatic, aromatic, or organosilicon group; and "w" and "z" are integers, where the value of "w" is between 1 and 40, the value of "z" is between 9 and 700. The coating can further comprise a polymer having a formula

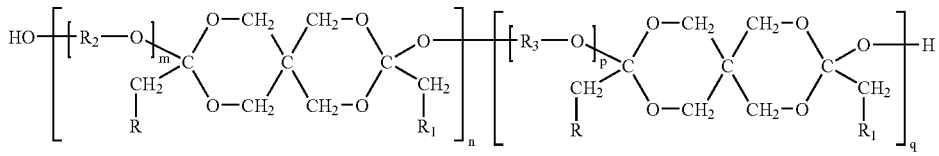

wherein $R_2$—O is a non-fouling moiety derived from a hydroxylated functional compound; $R_3$ is an aliphatic or cycloaliphatic group; "m," "n," "p," and "q" are all integers, where the value of "m" is between 5 and 500, the value of "n" is between 2 and 350, the value of "p" is between 1 and 20, and the value of "q" is between 10 and 550.

A method for fabricating a coating for an implantable medical device is provided. The method comprises applying a polymer onto the surface of the device, wherein the polymer comprises a product of co-polycondensation of a diketene acetal and a diol.

DETAILED DESCRIPTION

A coating for an implantable medical device, such as a stent, according to one embodiment of the present invention, can include an optional primer layer, a drug-polymer layer (also referred to as "reservoir" or "reservoir layer") or alternatively a polymer-free drug layer, an optional topcoat layer and an optional finishing coat layer. The drug-polymer layer serves as a reservoir for the drug. The reservoir layer or the polymer free drug layer can be applied directly onto the stent surface. The optional primer layer can be applied on the stent surface to improve the adhesion of the drug-polymer layer or the polymer free drug layer to the stent. The optional topcoat layer, which can be essentially free from any drugs, serves as a rate limiting membrane, which helps to control the rate of release of the drug. The optional finishing coat layer can be the outermost layer of the coating to provide the outermost surface of the coating with biocompatible, non-thrombogenic, hemocompatible, and/or non-fouling properties. A surface that does not adsorb proteins, or that adsorbs only a minimal amount of proteins, is herein referred to as "non-fouling" surface, and compounds or moieties making the surface non-fouling are is herein referred to as "non-fouling" compounds or moieties.

According to the present invention, polyorthoesters are polymers that can be used to make the stent coatings. The suitable polyorthoesters can be separated in two categories described below and summarized in Table 1.

TABLE 1

Polyorthoesters

| Category | Layer(s) of the Stent Coating | Monomeric Building Blocks |
|---|---|---|
| I | 1. primer layer<br>2. reservoir layer<br>3. topcoat layer | 1. diketene acetal<br>2. diol |
| II | 1. primer layer<br>2. reservoir layer<br>3. topcoat layer<br>4. finishing coat layer | 1. diketene acetal<br>2. diol<br>3. hydroxylated functional compound |

The Category I of polyorthoesters can be used for making any or all of the optional primer layer, the reservoir layer, and/or the optional topcoat layer. To obtain polyorthoesters of the Category I, at least one first monomeric building block comprising a diketene acetal is reacted with at least one second monomeric building block comprising a diol. The diol block can provide the polyorthoester with biocompatible, hemocompatible, non-thrombogenic, and/or non-fouling properties.

The Category II of polyorthoesters can be used for making any or all of the optional primer layer, the reservoir layer, the optional topcoat layer, and/or the optional finishing coat layer. To obtain polyorthoesters of the Category II, at least one first monomeric building block comprising a diketene acetal is reacted with at least one second monomeric building block comprising a diol, and at least one third monomeric building block comprising a hydroxylated functional compound. At least one of the diol and the hydroxylated functional compound can provide the polyorthoester with biocompatible, hemocompatible, non-thrombogenic, and/or non-fouling properties.

Representative examples of some monomers comprising the first, the second and the third monomeric blocks can be described as follows.

I. Diketene Acetals

Diketene acetals are monomeric building blocks that include two reactive centers capable of reacting with two hydroxy functional molecules, and therefore, can serve as linking agents. One family of diketene acetals that can be used include the compounds having a general formula (I):

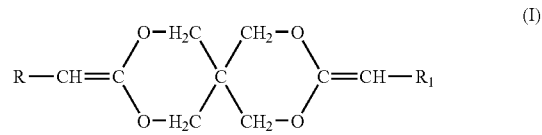

where R and $R_1$ are, independently, unsubstituted or substituted straight-chained, branched, or cyclic alkyl radicals $C_1$-$C_8$, or unsubstituted or substituted aryl radicals.

Other diketene acetals that can be used correspond to compounds having formula (II):

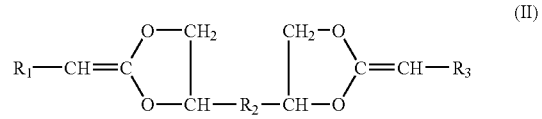

In diketene acetals described by formula (II), $R_1$ and $R_3$ is each, independently, unsubstituted or substituted straight-chained, branched, or cyclic alkyl radicals $C_1$-$C_8$, or unsubstituted or substituted aryl radicals; $R_2$ is a straight chain or branched $C_1$ to $C_{16}$ alkyl group, which can also contain ether groups.

Examples of particular diketene acetals that can be used include 3,9-diethylidene-2,4,8,10-tetraoxaspiro-[5,5]-undecane (DETOSU), 3,9-dipentylidene-2,4,8,10-tetraoxaspiro-

[5,5]-heptadecane (DPTOSH), 3,9-dibutylidene-2,4,8,10-tetraoxaspiro-[5,5]-pentadecane, 3,9-dipropylidene-2,4,8,10-tetraoxaspiro-[5,5]-tridecane, all described by formula (I) and mixtures thereof.

Formula (I) describes the molecule of DETOSU where both R and $R_1$ are methyl groups. Accordingly, DETOSU has the formula (III):

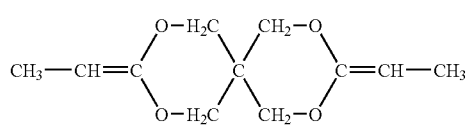

(III)

For DPTOSH, both R and $R_1$ are n-butyl groups.

II. Diols

Diol monomeric building blocks include short-to-moderate length aliphatic, cycloaliphatic, aromatic, or organosilicon diols or blends or combinations thereof. The diols can react with the diketene acetal to form hard segments of the polyorthoesters. The hard segments can either have some crystallinity, or have a $T_g$ above body temperature, e.g., in case of a human body, above about 37° C. The hard segments can serve as quasi cross-linking agents both strengthening the final polyorthoester and enabling the polyorthoester to behave as an elastomer.

Some example of diols that can be utilized include 1,4-butanediol, 1,6-hexanediol, trans-cyclohexanedimethanol, cis-cyclohexanedimethanol, and mixtures thereof. Examples of suitable mixtures include mixtures of either trans- or cis-cyclohexanedimethanol with 1,6-hexanediol. The mass ratio between 1,6-hexanediol and one of the cyclohexanedimethanols can be between about 10:90 and about 90:10, for example, about 65:35.

Examples of other aliphatic diols that can be used include $C_2$ through $C_{16}$ α,ω-alkylene glycols, for example, ethylene glycol ($C_2$), 1,2-propylene glycol ($C_3$), 1,5-pentanediol ($C_5$), 1,7-heptanediol ($C_7$), 1,8-octanediol ($C_8$), 1,9-nonanediol ($C_9$), 1,10-decanediol ($C_{10}$), 1,11-undecanediol ($C_{11}$), 1,12-dodecanediol ($C_{12}$), 1,13-tridecanediol ($C_{13}$), 1,14-tetradecanediol ($C_{14}$), 1,15-pentadecanediol ($C_{15}$), 1,16-hexadecanediol ($C_{16}$), or mixtures thereof. Other examples include alkylene glycols other than $C_2$ through $C_{16}$ α,ω-alkylene glycols, for example, 1,3-propylene glycol, butane-1,3-diol, pentane-2,4-diol, hexane-2,5-diol, or mixtures thereof. Yet other examples of aliphatic diols that can be used include poly- or oligoalkylene glycols such as diethylene glycol, triethylene glycol, tetraethylene glycol, poly(tetraethylene glycol), poly(pentaethylene glycol), poly(hexamethylene glycol), and mixtures thereof.

Examples of other cycloaliphatic diols that can be used include 1,2-cyclobutanediol, 1,3-cyclobutanediol, 1,2-cyclopentanediol, 1,3-cyclopentanediol, 1,2-cyclohexanediol, 1,3-cyclohexanediol, 1,4-cyclohexanediol, 1,2-cycloheptanediol, 1,3-cycloheptanediol, 1,4-cycloheptanediol, poly(caprolactone diol), and mixtures thereof.

Examples of suitable aromatic diols include p-(1,4), o-(1,2), and m-(1,3) benzenedimethanol, or mixtures thereof. 1,4-benzenedimethanol is also known as p-phenylene dicarbinol or-p-xylene-α,α' diol. 1,2-benzenedimethanol is also known as 1,2-bis(hydroxymethyl)benzene or phthalyl alcohol. One example of a suitable organosilicon diol includes a carbinol-terminated poly(dimethyl siloxane).

Diol monomeric building blocks can be described by a general formula (IV):

HO—$R_3$—OH      (IV)

where $R_3$ represents an aliphatic, cycloaliphatic, aromatic, or organosilicon group. For example, when compound (IV) is an alkylene glycol, $R_3$ is the poly- or oligomethylene structure $(CH_2)_y$, where "y" is an integer, having a value between 2 and 16. To illustrate, when compound (IV) is ethylene glycol, y=2. In case of propylene glycol, y=3.

III. Hydroxylated Functional Compounds

Hydroxylated functional compounds can be used for forming the optional finishing coat layer providing the outermost surface of the stent coating with non-fouling characteristics.

The hydroxylated functional compounds can react with the diketene acetal to form soft segments of polyorthoesters. The soft segments can have a glass transition temperature ($T_g$) below the body temperature, e.g., in case of humans, below about 37° C. The hydroxyl group can be located in a terminal or non-terminal position of the molecule. Examples of suitable hydroxylated functional compounds include poly(alkylene glycols), for example, poly(ethylene glycol) (PEG), poly(propylene glycol) (PPG) or poly(tetramethylene glycol), PLURONIC surfactants, hydroxylated poly(vinyl pyrrolidone), dextran, dextrin, hyaluronic acid and its derivatives such as sodium hyaluronate, and poly(2-hydroxyethyl methacrylate), hydroxy functional poly(styrene sulfonate), hydroxy functional phosphoryl choline methacrylate polymers, polymers with both hydroxyl and phosphoryl choline functionality, heparin, or mixtures thereof. PLURONIC is a trade name of poly(ethylene oxide-co-propylene oxide) and is available from BASF Corp. of Parsippany, N.J. A molecular weight of a suitable hydroxylated functional compound can be such so as to allow passage of the released molecule through the kidneys, for example, below 40,000 Daltons, such as between about 300 and 20,000 Daltons.

Suitable hydroxylated functional compounds can be described by a general formula (V):

HO[—$R_2$—O—]$_m$H,      (V)

where "m" is an integer, and —$R_2$—O— represents the moiety of compound (V) providing for non-fouling characteristics. For example, when compound (V) is a poly(alkylene glycol), $R_3$ is the polymethylene structure $(CH_2)_x$, where "x" is an integer. To illustrate, when compound (V) is PEG, x=2.

To prepare polyorthoesters of Category I described above, to be used for fabricating any or all of the optional primer layer, the reservoir layer, and/or the optional topcoat layer, a diketene acetal, or a blend of more than one diketene acetal, can be reacted with a diol, or a blend of more than one diol. This reaction can be carried out at a temperature between ambient and about 80° C., for example, between about 40° C. and about 70° C., in the presence of an acid catalyst such as p-toluenesulfonic acid. As a result, a polyorthoester having a general formula (VI) can be obtained

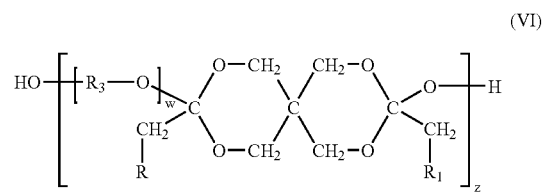

(VI)

where R, $R_1$, and $R_3$ are as described above; "w" and "z" are integers, where the value of "w" is between 1 and 40, and the value of "z" is between 9 and 700.

To prepare polyorthoesters of Category II described above, to be used for fabricating of the optional finishing coat layer, a two-step synthetic process can be used. The first step includes reacting the whole amount of a diketene acetal, or a mixture of more than one diketene acetals, with a hydroxylated functional compound or a mixture of more than one hydroxylated functional compounds. The reaction ("reaction 1") can be conducted in anhydrous environment and the temperature can be between ambient temperature and about 80° C., for example, about 70° C. Reaction 1 can be catalyzed by a strong base or acid such as p-toluenesulfonic acid. The second step includes adding a diol or a mixture of more than one diol to the product of reaction 1, and the temperature at which the second step can be conducted can be also between ambient temperature and about 80° C., for example, about 70° C. As a result of the two-step process described above, a polyorthoester can be obtained, the polyorthoester having a general formula (VII):

polyvinylidene chloride), polyacrylonitrile, polyvinyl ketones, polyvinyl aromatics (such as polystyrene), polyvinyl esters (such as polyvinyl acetate), copolymers of vinyl monomers with each other and olefms (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, other polycarbonates, polyoxymethylenes, polyimides, polyethers, epoxy resins, other polyurethanes, rayon, rayon-triacetate, cellulose, cellulose acetate, cellulose butyrate, cellulose acetate butyrate, cellophane, cellulose nitrate, cellulose propionate, cellulose ethers, soluble fluorinated polymers and carboxymethyl cellulose.

The stent, or other implantable medical device can be used in any part of the vascular system, including neurological, carotid, coronary, renal, aortic, iliac, femoral or any other part

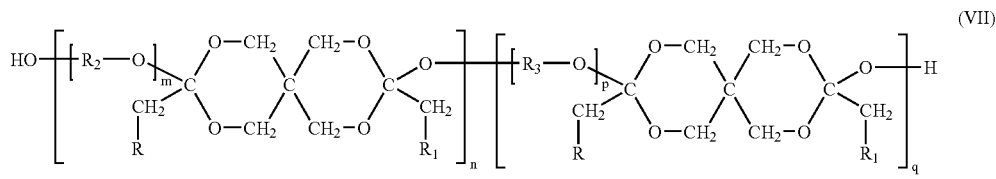

where R, $R_1$, $R_2$, and $R_3$ are as described above; "m," "n," "p," and "q" are all integers, where the value of "m" is between 5 and 500, the value of "n" is between 2 and 350, the value of "p" is between 1 and 20, and the value of "q" is between 10 and 550. The polyorthoester described by formula (VI) can have molecular weight within a range of between about 20,000 and about 200,000 Daltons.

Polyorthoesters of this invention can be used for making stent coatings. The coating can be applied onto the stent by a commonly used method known to one of ordinary skill in the art, for instance, by spraying, dipping or molding. The polyorthoesters can be used alone or in combination with other suitable polymers. Poly(ethylene-co-vinyl alcohol) (EVAL) is one example of a polymer than can be employed for combining with polyorthoesters. EVAL is a product of hydrolysis of ethylene-vinyl acetate copolymers and may also be a terpolymer including up to 5 molar % of units derived from styrene, propylene and other suitable unsaturated monomers. EVAL is available from Sigma-Aldrich Co. of Milwaukee, Wis.

Representative examples of other polymers that can be combined with polyorthoesters include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(L-lactide), poly(D,L-lactide), poly(glycolide), poly(glycolic acid-co-trimethylene carbonate), polyphosphoester, polyphosphoester urethane; poly(amino acids), cyanoacrylates, poly(trimethylene carbonate), poly(iminocarbonate), co-poly(ether-esters) (e.g. PEO/PLA), poly(ester-amides), polyalkylene oxalates, polyphosphazenes, biomolecules (such as fibrin, fibrinogen, cellulose, starch, collagen and hyaluronic acid), polyurethanes, silicones, polyesters, polyolefms, polyisobutylene and ethylene-alphaolefin copolymers, acrylic polymers and copolymers, vinyl halide polymers and copolymers (such as polyvinyl chloride), poly(vinylidene fluoride-co-hexafluoropropene), polyvinyl ethers (such as polyvinyl methyl ether), polyvinylidene halides (such as polyvinylidene fluoride and of the peripheral vasculature. The are no limitations on the size of the stent, its length, diameter, strut thickness or pattern. Examples of such implantable devices include self-expandable stents, balloon-expandable stents, stent-grafts, grafts (e.g., aortic grafts). The coating can also be used with artificial heart valves, cerebrospinal fluid shunts, coronary shunts, pacemaker electrodes, and endocardial leads (e.g., FINELINE and ENDOTAK, available from Guidant Corporation). The underlying structure of the device can be of virtually any design. The device can be made of a metallic material or an alloy such as, but not limited to, cobalt chromium alloy (ELGILOY), cobalt chromium alloy L-605, stainless steel (316L),"MP35N," "MP20N," ELASTINITE (Nitinol), tantalum, nickel-titanium alloy, platinum-iridium alloy, gold, magnesium, or combinations thereof. "L-605" alloy consists of 50% cobalt, 20% chromium, 15% tungsten, 10% nickel, 3% iron, and 1.5% manganese. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

The drug can include any substance capable of exerting a therapeutic or prophylactic effect for a patient. The drug may include small molecule drugs, peptides, proteins, oligonucleotides, and the like. The drug could be designed, for example, to inhibit the activity of vascular smooth muscle cells. It can be directed at inhibiting abnormal or inappropriate migration and/or proliferation of smooth muscle cells to inhibit restenosis.

Examples of drugs include antiproliferative substances such as actinomycin D, or derivatives and analogs thereof (manufactured by Sigma-Aldrich, or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

The following examples demonstrate some embodiments of the present invention.

EXAMPLE 1

Synthesis of 3,9-diethylidene-2,4,8,10-tetraoxaspriro-[5.5]-undecane (DETOSU)

Diketene acetals can be prepared by several techniques. One method known in the art is the condensation of an appropriate polyhydroxy compound, such as pentaerythritol, with two equivalents of a 2-halocarboxyaldehyde dialkyl acetal, followed by dehydrohalogentaion to yield the diketene acetal. This reaction is described by Corey et al., *J. Org. Chem.*, 38, 3224 (1973).

Diketene acetals can also be prepared by the isomerization of divinyl acetals. For example, to a 1 liter vessel equipped with a magnetic stirrer, argon inlet and thermocouple, 400 ml of ethylene diamine can be added. The vessel can be immersed in ice water and kept below 4° C. with a steady stream of argon being directed into the flask. A solution containing about 45 g (0.7 moles) of n-butyllithium in hexane can be added to ethylene diamine via gas tight syringe in a syringe pump over one hour. A solution containing about 175 g (0.83 moles) of 3,9-divinyl-2,4,8,10-tetraoxaspiro[5.5]undecane dissolved in about 170 ml of ethylene diamine can be cooled to about 4° C. and added to the vessel. 3,9-divinyl-2,4,8,10-tetraoxaspiro[5.5]undecane is available from Aldrich Chemical Company, Inc. of Milwaukee, Wis. After agitation at about 4° C. for about four hours, the reaction mixture can be poured onto about 2 liters of ice water with vigorous stirring.

The resulting solution can be extracted with two 500 ml portions of hexane. The hexane extracts can be combined, and further extracted with three 500 ml portions of water, After drying over anhydrous magnesium sulfate, and suction filtration, the filtrate can be evaporated to dryness yielding crude 3,9-diethylidene-2,4,8,10 tetraoxaspiro[5.5] undecane (DETOSU). DETOSU can be used for synthesizing polyorthoesters as described in Examples 2 and 4 below.

EXAMPLE 2

Synthesis of Poly(3,9-diethylidene-2,4,8,10-tetraoxaspiro-[5,5]-undecane-co-cyclohexanedimethanol-co-1,6-hexanediol) (DETOSU-CHD-HD)

A 250 ml, three necked flask can be equipped with a magnetic stirrer, reflux condenser with rubber septum containing an argon inlet, argon outlet, and addition septum. The following reagents can be charged into this flask:

(a) about 15 g (0.1042 moles) trans-cyclohexanedimethanol;

(b) about 12.29 g (0.1042 moles) 1,6-hexanediol; and (c) about 50 g anhydrous tetrahydrofuran (THF).

Using a cannula, a solution of about 44.18 g (0.2084 moles) of DETOSU, synthesized as explained in Example 1, in about 50 g of THF can be added to the flask by applying positive argon pressure. About ten drops of a solution of p-toluenesulfonic acid in THF (the concentration can be about 10 mg/ml) can be added and the mixture allowed to stir without heating for one hour. The solution can be slowly poured into 3 liters of methanol containing about 100 parts per million (ppm) of triethylamine, to yield the polyorthoester DETOSU-CHD-HD that can be isolated by filtration.

EXAMPLE 3

Synthesis of 3,9-dipentylidene-2,4,8,10-tetraoxaspiro [5.5]heptadecane (DPTOSH)

To a 1 liter vessel equipped with a magnetic stirrer, argon inlet and thermocouple, about 400 ml of ethylene diamine can be added. The vessel can be immersed in ice water and kept below 4° C. with a steady stream of argon into the flask. A solution containing about 45 g (0.7 moles) of n-butyllithium in hexane can be added to ethylene diamine via gas tight syringe in a syringe pump over one hour. A solution containing about 245.7 g (0.83 moles) of 3,9-di(1-pentene)-2,4,8,10-tetraoxaspiro[5.5]heptadecane dissolved in about 170 ml of ethylene diamine can be cooled to about 4° C. and added to the vessel. After agitation at about 4° C. for about four hours, the reaction mixture can be poured onto about 2 liters of ice water with vigorous stirring.

The resulting solution can be extracted with two 500 ml portions of hexane. The hexane extracts can be combined, and further extracted with three 500 ml portions of water. After drying over anhydrous magnesium sulfate, and suction filtration, the filtrate can be evaporated to dryness yielding crude 3,9-diethylidene-2,4,8,10-tetraoxaspiro[5.5]undecane (DPTOSH). DPTOSH can be used for synthesizing polyorthoesters. For example, DPTOSH can replace a part or all DETOSU to make polyorthoesters similar to those as described in Examples 2 and 4.

EXAMPLE 4

Synthesis of Poly(ethylene glycol-co-3,9-diethylidene-2,4,8,10-tetraoxaspiro-[5,5]-undecane-co-propylene glycol) (PEG-DETOSU-PG)

About 25 g (25 mmol) of PEG having molecular weight ($M_n$) of about 1,000 can be placed in a 1-liter round bottom flask equipped with a mechanical stirrer. PEG can be treated to remove water by being heated to about 80° C. using an oil bath, while being stirred under vacuum of about 25 mm Hg. About 400 g of tetrahydrofuran (THF) and about 27.83 g (131 mmol) of DETOSU can be added to the flask and dissolved with continued stirring. A solution of p-toluenesulfonic acid in THF having concentration of about 25 g/l can be prepared and about 15 drops of this solution can be added to the contents of the flask. The stirring can continue for about 1 hour while the contents of the flask are maintained at about 80° C. About 8.08 g (106 mmol) of propylene glycol can then be added to the flask, and the stirring can be continued for about 1 more hour while the contents of the flask are kept at about 80° C. The reaction mixture then can be cooled and about 1 liter of hexane can be added. As a result, the polyorthoester PEG-DETOSU-PG, can be collected by filtration. The polymer can then be purified by dissolution in dry methanol and precipitation with hexane. The ratio between the soft and hard segments in the polymer is about 1:1 by mass.

EXAMPLE 5

Synthesis of Poly(3,9-diethylidene-2,4,8,10-tetraoxaspiro-[5,5]-undecane-co-1,6-hexanediol) (DETOSU-HD)

DETOSU synthesized as described in Example 1 can be dissolved in THF. The solution can contain 27.83 g (131 mmol) of DETOSU and about 400 g of THF. The DETOSU/THF solution can be combined in a flask with about 10 drops of the solution of p-toluenesulfonic acid described in Example 1 and the mixture can be stirred for about 1 hour while the contents of the flask are maintained at about 80° C. An equimolar amount (about 131 mmol or 15.20 g) of 1,6-hexanediol (HD) can then be added to the flask, and the stirring can continue for about 1 more hour while the contents of the flask are kept at about 80° C. The reaction mixture then can be cooled and about 1 liter of hexane can be added. As a result, the polyorthoester DETOSU-HD, can be collected by filtration.

EXAMPLE 6

Synthesis of Poly(ethylene glycol-co-3,9-diethylidene-2,4,8,10-tetraoxaspiro-[5,5]-undecane-co-cyclohexanedimethanol) (PEG-DETOSU-CHD)

About 25 g (83.3 mol) of PEG having molecular weight ($M_n$) of about 300 can be placed into a 1 liter round bottom flask equipped with a mechanical stirrer. PEG can be treated to remove water by being heated to about 80° C. using an oil bath, while being stirred under vacuum of about 25 mm Hg. About 400 g of tetrahydrofuran (THF) and about 35.39 g (166.6 mmol) of DETOSU can be added to the flask and dissolved with continued stirring. A solution of p-toluenesulfonic acid in THF having concentration of about 25 g/l can be prepared and about 15 drops of this solution can be added to the contents of the flask. The stirring can continue for about 1 hour while the contents of the flask are maintained at about 80° C. About 9.82 g (83.3 mmol) of cyclohexanedimethanol can then be added to the flask, and the stirring can be continued for about 1 more hour while the contents of the flask are kept at about 80° C. The reaction mixture then can be cooled and about 1 liter of hexane can be added. As a result, the polyorthoester PEG-DETOSU-CHD, can be collected by filtration. The polymer can then be purified by dissolution in dry methanol and precipitation with hexane. The molar ratio between the units derived from PEG, DETOSU, and CHD is about 1:2:1.

EXAMPLE 7

A first composition can be prepared by mixing the following components:

(a) about 2.0 mass % the DETOSU-HD polyorthoester obtained as described in Example 5; and (b) the balance, a blend of THF and xylene at a mass ratio of THF to xylene of about 3:1.

The first composition can be applied onto the surface of a bare 12 mm VISION stent (available from Guidant Corp.) by spraying and dried to form a primer layer. An EFD spray head can be used, having a 0.014 inch round nozzle tip and a 0.028 inch round air cap with a feed pressure of about 0.2 atm (3 psi) and an atomization pressure of between about 1 atm and 1.3 atm (15 to 20 psi). The total amount of solids of the primer layer can be about 50 micrograms (µg). After spraying, the stent can be baked at about 60° C. for about one hour. "Solids" means the amount of dry residue deposited on the stent after all volatile organic compounds (e.g. the solvent) have been removed.

A second composition can be prepared by mixing the following components:

(a) about 2 mass % DETOSU-CHD-HD polyorthoester synthesized as described in Example 2;

(b) about 1 mass % EVEROLIMUS; and (c) the balance, a blend of THF and xylene at a mass ratio of THF to xylene of about 3:1.

The second composition can be applied onto the dried primer to form a reservoir layer, using the same spraying technique and equipment used for the primer layer. The solvent can be removed by baking at about 50° C. for about one hour. The total amount of solids of the drug polymer layer can be about 200 µg.

A third composition can be prepared by mixing the following components:

(a) about 2 mass % DETOSU-CHD-HD polyorthoester synthesized as described in Example 2; and (b) the balance, a solvent blend of THF and xylene at a mass ratio of THF to xylene of about 3:1.

The third composition can be applied onto the dried reservoir layer to form a topcoat layer. The solvent can be removed by baking at 50° C. for one hour. The total amount of solids of the topcoat layer can be about 100 µg.

EXAMPLE 8

A first composition can be prepared by mixing the following components:

(a) about 2.0 mass % poly(ethylene-co-vinyl alcohol) having about 44 mole % units derived from ethylene; and (b) the balance, a blend of THF and dimethylacetamide (DMAC) at a mass ratio of THF to DMAC of about 1:2

The first composition can be applied onto the surface of a bare 12 mm VISION stent by spraying as described in Example 7, and dried to form a primer layer. After spraying, the stent can be baked at about 130° C. for about one hour. The total amount of solids of the primer layer can be about 50 µg.

A second composition can be prepared by mixing the following components:

(a) about 2 mass % DETOSU-CHD-HD polyorthoester synthesized as described in Example 2;

(b) about 1 mass % SIROLIMUS; and (c) the balance, a blend of THF and xylene at a mass ratio of THF to xylene of about 3:1.

The second composition can be applied onto the dried primer to form a reservoir layer, using the same spraying technique and equipment used for the primer layer. Solvent can be removed by baking at about 50° C. for about one hour. The total amount of solids of the drug polymer layer can be about 125 µg.

A third composition can be prepared by mixing the following components:

(a) about 2 mass % DETOSU-CHD-HD polyorthoester synthesized as described in Example 2;

(b) the balance, a solvent blend of THF and xylene at a mass ratio of THF to xylene of about 3:1.

The third composition can be applied onto the dried reservoir layer to form a topcoat layer. The solvent can be removed by baking at 50° C. for one hour. The total amount of solids of the topcoat layer can be about 100 µg.

EXAMPLE 9

A first composition can be prepared by mixing the following components:

(a) about 2.0 mass % DETOSU-HD polyorthoester obtained as described in Example 5; and (b) the balance, a blend of THF and xylene at a mass ratio of THF to xylene of about 3:1.

The first composition can be applied onto the surface of a bare 12 mm VISION stent by spraying as described in Example 7, and dried to form a primer layer. After spraying, the stent can be baked at about 60° C. for about one hour. The total amount of solids of the primer layer can be about 50 µg.

A second composition can be prepared by mixing the following components:

(a) about 2 mass % DETOSU-CHD-HD polyorthoester synthesized as described in Example 2;

(b) about 1 mass % EVEROLIMUS; and (c) the balance, a blend of THF and xylene at a mass ratio of THF to xylene of about 3:1.

The second composition can be applied onto the dried primer to form a reservoir layer, using the same spraying technique and equipment used for the primer layer. The solvent can be removed by baking at about 50° C. for about one hour. The total amount of solids of the drug polymer layer can be about 200 µg.

A third composition can be prepared by mixing the following components:

(a) about 2 mass % DETOSU-CHD-HD polyorthoester synthesized as described in Example 2;

(b) the balance, a solvent blend of THF and xylene at a mass ratio of THF to xylene of about 3:1.

The third composition can be applied onto the dried reservoir layer to form a topcoat layer. Solvent can be removed by baking at 50° C. for one hour. The total amount of solids of the topcoat layer can be about 100 µg.

A fourth composition can be prepared by mixing the following components:

(a) about 2 mass % PEG-DETOSU-CHD polyorthoester obtained as described in Example 6; and (b) the balance, a solvent blend of chloroform and 1,1,2-tricholroethane (TCE) at a mass ratio of chloroform to TCE of about 1:3.

The fourth composition can be applied onto the dried topcoat layer to form a finishing coat layer. The solvent can be removed by baking at 50° C. for one hour. The total amount of solids of the finishing coat layer can be about 150 µg.

EXAMPLE 10

A first composition can be prepared by mixing the following components:

(a) about 2.0 mass % poly(ethylene-co-vinyl alcohol) having about 44 mole % units derived from ethylene; and (b) the balance, a blend of THF and dimethylacetamide (DMAC) at a mass ratio of THF to DMAC of about 1:2

The first composition can be applied onto the surface of a bare 12 mm VISION stent by spraying as described in Example 7, and dried to form a primer layer. After spraying, the stent can be baked at about 130° C. for about one hour. The total amount of solids of the primer layer can be about 50 µg.

A second composition can be prepared by mixing the following components:

(a) about 2 mass % DETOSU-CHD-HD polyorthoester synthesized as described in Example 2;

(b) about 0.2 mass % PACLITAXEL; and (c) the balance, a blend of THF and xylene at a mass ratio of THF to xylene of about 3:1.

The second composition can be applied onto the dried primer to form a reservoir layer, using the same spraying technique and equipment used for the primer layer. The solvent can be removed by baking at about 50° C. for about one hour. The total amount of solids of the drug polymer layer can be about 125 µg.

A third composition can be prepared by mixing the following components:

(a) about 2 mass % DETOSU-CHD-HD polyorthoester synthesized as described in Example 2; and (b) the balance, a solvent blend of THF and xylene at a mass ratio of THF to xylene of about 3:1.

The third composition can be applied onto the dried reservoir layer to form a topcoat layer. The solvent can be removed by baking at 50° C. for about one hour. The total amount of solids of the topcoat layer can be about 100 µg.

A fourth composition can be prepared by mixing the following components:

(a) about 2 mass % PEG-DETOSU-CHD polyorthoester obtained as described in Example 6; and (b) the balance, a solvent blend of chloroform and 1,1,2-trichloroethane (TCE) at a mass ratio of chloroform to TCE of about 1:3.

The fourth composition can be applied onto the dried topcoat layer to form a finishing coat layer. The solvent can be removed by baking at 50° C. for about one hour. The total amount of solids of the finishing coat layer can be about 150 µg.

EXAMPLE 11

A first composition can be prepared by mixing the following components:

(a) about 2.0 mass % DETOSU-HD polyorthoester obtained as described in Example 5; and (b) the balance, a blend of THF and xylene at a mass ratio of THF to xylene of about 3:1.

The first composition can be applied onto the surface of a bare 12 mm VISION stent by spraying as described in Example 7, and dried to form a primer layer. After spraying, the stent can be baked at about 60° C. for about one hour. The total amount of solids of the primer layer can be about 50 μg.

A second composition can be prepared by mixing the following components:
(a) about 2 mass % DETOSU-CHD-HD polyorthoester synthesized as described in Example 2;
(b) about 1 mass % EVEROLIMUS; and
(c) the balance, a blend of THF and xylene at a mass ratio of THF to xylene of about 3:1.

The second composition can be applied onto the dried primer to form a reservoir layer, using the same spraying technique and equipment used for the primer layer. The solvent can be removed by baking at about 50° C. for about one hour. The total amount of solids of the drug polymer layer can be about 200 μg.

A third composition can be prepared by mixing the following components:
(a) about 2 mass % DETOSU-CHD-HD polyorthoester synthesized as described in Example 2; and
(b) the balance, a solvent blend of THF and xylene at a mass ration of THF to xylene of about 3:1.

The third composition can be applied onto the dried reservoir layer to form a topcoat layer. The solvent can be removed by baking at 50° C. for about one hour. The total amount of solids of the topcoat layer can be about 100 μg.

A fourth composition can be prepared by mixing the following components:
(a) about 2 mass % of poly(ethylene glycol-terephtalate-co-butylene terephthalate) having a mass ratio between units derived from ethylene glycol-terephthalate and units derived from 1,4-butanediol terephthalate of about 11:9; and
(b) the balance, a solvent blend of chloroform and 1,1,2-trichloroethane (TCE) at a mass ratio of chloroform to TCE of about 1:4.

The fourth composition can be applied onto the dried reservoir layer to form a finishing coat layer. The solvent can be removed by baking at 50° C. for about one hour. The total amount of solids of the finishing coat layer can be about 150 μg.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical article, comprising an implantable substrate having a coating deposited on the substrate, the coating comprising a polymer, the polymer being a product of co-polycondensation of a diketene acetal and a diol, wherein the diol comprises, cycloaliphatic, aromatic, or organosilicon diols or blends or combinations thereof where the diketene acetal has a structure of formula (I) or the diol comprises cycloaliphatic, aromatic, or organosilicon diols or blends or combinations thereof where the diketene acetal has a structure of formula (II), wherein the diketene acetal is selected from a group of compounds having formulae (I) or (II):

$$R-CH=C\underset{O-CH_2}{\overset{O-CH_2}{<}}\underset{CH_2-O}{\overset{CH_2-O}{>}}C=CH-R_1 \quad (I)$$

$$R_1-CH=C\underset{O-CH-R_2-CH-O}{\overset{O-CH_2\qquad CH_2-O}{<}}C=CH-R_3 \quad (II)$$

wherein:
R, $R_1$, and $R_3$ are, independently, unsusbstituted or substituted straight-chained, branched, or cyclic alkyl radicals $C_1$-$C_8$, or unsusbstituted or substituted aryl radicals;
$R_2$ is a straight chain or branched $C_1$ to $C_{16}$ alkyl group or a straight chain or branched $C_1$ to $C_{16}$ alkyl group containing an ether group;
R and $R_1$ are selected such that the diketene acetal is one of 3,9-dipentylidene-2,4,8,10-tetraoxaspiro-[5,5]-heptadecane, 3,9-dibutylidene-2,4,8,10-tetraoxaspiro-[5,5]-pentadecane, 3,9-dipropylidene-2,4,8,10-tetraoxaspiro-[5,5]-tridecane, and mixtures thereof;
wherein the cycloaliphatic diols are selected from a group consisting of 1,2-cyclobutanediol, 1,3-cyclobutanediol, 1,2-cyclopentanediol, 1,3-cyclopentanediol, 1,2-cyclohexanediol, 1,3-cyclohexanediol, 1,2-cycloheptanediol, 1,3-cycloheptanediol, 1,4-cycloheptanediol, caprolactone diol, and mixtures thereof; and
wherein the aromatic diols are selected from a group consisting of o-benzenedimethanol, m-benzenedimethanol, and mixtures thereof.

2. The article of claim 1, wherein the implantable substrate is a stent.

3. The article of claim 1, wherein the diketene acetal is selected from a group of compounds having formula (II)

$$R_1-CH=C\underset{O-CH-R_2-CH-O}{\overset{O-CH_2\qquad CH_2-}{<}}C=CH-R_3. \quad (II)$$

4. The article of claim 1, wherein the diol is a cycloaliphatic diol selected from a group consisting of 1,2-cyclobutanediol, 1,3-cyclobutanediol, 1,2-cyclopentanediol, 1,3-cyclopentanediol, 1,2-cyclohexanediol, 1,3-cyclohexanediol, 1,2 cyclohexanediol, 1,3-cycloheptanediol, 1,4-cycloheptanediol, caprolactone diol, and mixtures thereof.

5. The article of claim 1, wherein the diol is an aromatic diol selected from a group consisting of, o-benzenedimethanol, m-benzenedimethanol, and mixtures thereof.

6. The article of claim 1, wherein the diol is an organosilicon diol comprising carbinol-terminated poly(dimethyl siloxane).

7. The article of claim 1, wherein a hydroxylated functional polymer compound is additionally included in the polycondensation process.

8. The article of claim 7, wherein the hydroxylated functional polymer compound comprises poly(alkylene glycols), hydroxylated poly(N-vinyl pyrrolidone), dextran, dextrin, hyaluronic acid, derivatives of hyaluronic acid, poly(2-hydroxyethyl methacrylate), hydroxy functional poly(styrene sulfonate), hydroxy functional phosphoryl choline methacrylate polymers, polymers with both hydroxyl and phosphoryl choline functionality, heparin, or mixtures thereof.

9. The article of claim 8, wherein the poly(alkylene glycols) are selected from a group consisting of poly(ethylene glycol), poly(propylene glycol), poly(tetramethylene glycol), and poly(ethylene oxide-co-propylene oxide).

10. A medical device, comprising a coating, the coating comprising a polymer including a unit having a formula:

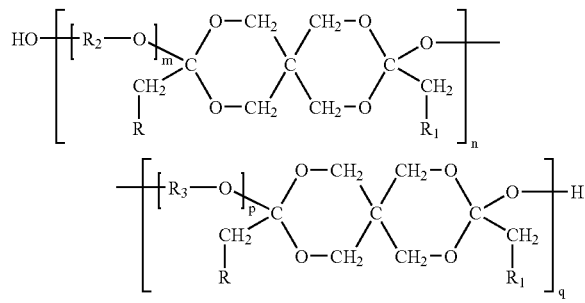

wherein:
R R$_1$ are, independently, unsusbstituted or substituted straight-chained, branched, or cyclic alkyl radicals C$_1$-C$_8$, or unsusbstituted or substituted aryl radicals;

R$_3$ is, cycloaliphatic, aromatic, or organosilicon group; and

"w" and "z" are integers, where the value of "w" is between 1 and 40, the value of "z" is between 9 and 700;

wherein the cycloaliphatic group is selected from a group consisting of 1,2-cyclobutane, 1,3-cyclobutane, 1,2-cyclopentane, 1,3-cyclopentane, 1,2-cyclohexane, 1,3-cyclohexane, 1,2-cycloheptane, 1,3-cycloheptane, 1,4-cycloheptane, caprolactone, and mixtures thereof; and wherein the aromatic group is selected from a group consisting of o-benzenedimethane, m-benzenedimethane, and mixtures thereof.

11. A method for fabricating a coating for an implantable medical device, the method comprising applying a polymer onto the surface of the device, wherein the polymer comprises a product of co-polycondensation of a diketene acetal and a diol, wherein the diol comprises, cycloaliphatic, aromatic, or organosilicon diols or blends or combinations thereof where the diketene acetal has a structure of formula (I) or the diol comprises cycloaliphatic, aromatic, or organosilicon diols or blends or combinations thereof where the diketene acetal has a structure of formula (II), wherein the diketene acetal is selected from a group of compounds having formulae (I) or (II):

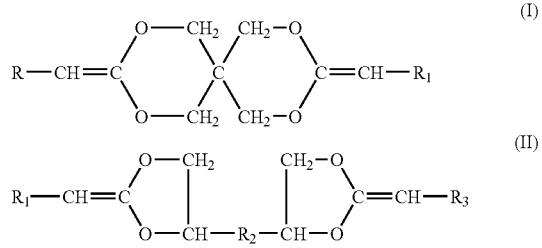

wherein:
R, R$_1$, and R$_3$ are, independently, unsusbstituted or substituted straight-chained, branched, or cyclic alkyl radicals C$_1$-C$_8$, or unsusbstituted or substituted aryl radicals;

R$_2$ is a straight chain or branched C$_1$ to C$_{16}$ alkyl group or a straight chain or branched C$_1$ to C$_{16}$ alkyl group containing an ether group; and R and R$_1$ are selected such that the diketene acetal is one of 3,9-dipentylidene-2,4,8,10-tetraoxaspiro-[5,5]-heptadecane, 3,9-dibutylidene-2,4,8,10-tetraoxaspiro-[5,5]-pentadecane, 3,9-dipropylidene-2,4,8,10-tetraoxaspiro-[5,5]-tridecane, and mixtures thereof;

wherein the cycloaliphatic diols are selected from a group consisting of 1,2-cyclobutanediol, 1,3-cyclobutanediol, 1,2-cyclopentanediol, 1,3-cyclopentanediol, 1,2-cyclohexanediol, 1,3-cyclohexanediol, 1,2-cycloheptanediol, 1,3-cycloheptanediol, 1,4-cycloheptanediol, caprolactone diol, and mixtures thereof; and wherein the aromatic diols are selected from a group consisting of o-benzenedimethanol, m-benzenedimethanol, and mixtures thereof.

12. The method of claim 11, wherein the medical device is a stent.

13. The method of claim 11, wherein the diketene acetal is selected from a group of compounds having formula (II)

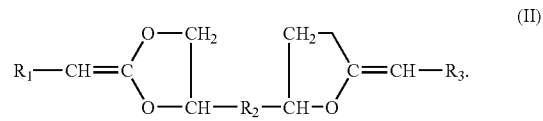

14. The method of claim 11, wherein the diol is a cycloaliphatic diol selected from a group consisting of 1,2-cyclobutanediol, 1,3-cyclobutanediol, 1,2-cyclopentanediol, 1,3-cyclopentanediol, 1,2-cyclohexanediol, 1,3-cyclohexanediol, 1,2-cycloheptanediol, 1,3-cycloheptanediol, 1,4-cycloheptanediol, caprolactone diol, and mixtures thereof.

15. The method of claim 11, wherein the diol is an aromatic diol selected from a group consisting of, o-benzenedimethanol, m-benzenedimethanol, and mixtures thereof.

16. The method of claim 11, wherein the diol is an organosilicon diol comprising carbinol-terminated poly(dimethyl siloxane).

17. The method of claim 11, wherein a hydroxylated functional polymer compound is additionally included in the polycondensation process.

18. The method of claim 17, wherein the hydroxylated functional polymer compound comprises poly(alkylene glycols), hydroxylated poly(N-vinyl pyrrolidone), dextran, dextrin, hyaluronic acid, derivatives of hyaluronic acid, poly(2-hydroxyethyl methacrylate), hydroxy functional poly(styrene sulfonate), hydroxy functional phosphoryl choline methacrylate polymers, polymers with both hydroxyl and phosphoryl choline functionality, heparin, or mixtures thereof.

19. The method of claim 18, wherein the poly(alkylene glycols) are selected from a group consisting of poly(ethylene glycol), poly(propylene glycol), poly(tetramethylene glycol), and poly(ethylene oxide-co-propylene oxide).

* * * * *